United States Patent [19]

Kelly et al.

[11] Patent Number: 4,954,080
[45] Date of Patent: Sep. 4, 1990

[54] CERAMIC ORTHODONTIC APPLIANCE

[75] Inventors: John S. Kelly, Temple City; Henrick K. Gille, Van Nuys, both of Calif.

[73] Assignees: Unitek Corporation, Monrovia; Ceradyne, Inc., Costa Mesa, both of Calif.

[21] Appl. No.: 248,297

[22] Filed: Sep. 21, 1988

Related U.S. Application Data

[63] Continuation of Ser. No. 861,240, May 8, 1986, abandoned.

[51] Int. Cl.$^5$ .............................................. A61C 3/00
[52] U.S. Cl. ...................................................... 433/8
[58] Field of Search ...................... 433/8, 9, 10, 18, 24; 264/16; 423/633

[56] References Cited

U.S. PATENT DOCUMENTS

| | | | |
|---|---|---|---|
| 1,976,141 | 10/1934 | Richardson | 433/8 |
| 2,045,025 | 6/1936 | Richardson | 433/8 |
| 2,926,422 | 3/1960 | Wallshein | 433/8 |
| 3,026,177 | 3/1962 | Pierre et al. | 423/625 |
| 3,026,210 | 3/1962 | Coble | 501/153 |
| 3,181,240 | 5/1965 | Kerhart et al. | 433/203.1 |
| 3,256,602 | 6/1966 | Broussard et al. | 433/13 |

(List continued on next page.)

FOREIGN PATENT DOCUMENTS

| | | |
|---|---|---|
| 0099741 | 2/1984 | European Pat. Off. . |
| 0160481 | 11/1985 | European Pat. Off. . |
| 0161831 | 11/1985 | European Pat. Off. . |
| 1228754 | 11/1966 | Fed. Rep. of Germany . |
| 1541219 | 6/1970 | Fed. Rep. of Germany . |
| 2039226 | 3/1971 | Fed. Rep. of Germany . |
| 2328213 | 1/1974 | Fed. Rep. of Germany . |
| 2554145 | 6/1977 | Fed. Rep. of Germany . |
| 2913509 | 2/1980 | Fed. Rep. of Germany . |
| 1083769 | 9/1967 | United Kingdom ................ 433/201 |

OTHER PUBLICATIONS

Some Optical, Thermo-Optical, and Piezo-Optical Properties of Synthetic Sapphire, M. A. Jeppesen, Journal of the Optical Society of America, vol. 48, No. 9, Sep. 1958, pp. 629 to 632.

Refraction and Dispersion of Synthetic Sapphire, I. H. Malitson, Journal of the Optical Society of America, vol. 52, No. 12, Dec., 1962, pp. 1377 to 1379.

Hot-Working of Aluminum Oxide: II, Optical Properties, W. H. Rhodes, et al., Journal of the American Ceramic Society, vol. 58, No. 1-2, pp. 31 to 34.

Fabrication of Translucent $Al_2O_3$ by High Pressure Sintering; Y. Ishitobi, et al. Ceramic Bulletin, vol. 56, No. 6 (1977), pp. 556–558.

Paper By C. A. Bruch, Preparation of Translucent Alumina From Powder; pp. 1 to 19.

Table 2.16. Physical and Chemical Characteristics of Sapphire; W. H. Kohl; Handbook of Materials and Techniques for Vacuum Devices, p. 86.

Table 3-2, Physical, Mechanical, Thermal, and Electrical Properties of Alumina, Chemical Rubber Company Handbook of Materials Science, C. T. Lynch, 1974, pp. 358-361.

*Primary Examiner*—John J. Wilson
*Attorney, Agent, or Firm*—Donald M. Sell; Walter N. Kirn; James D. Christoff

[57] ABSTRACT

An orthodontic bracket or similar orthodontic appliance is made of a polycrystalline ceramic having a translucency which minimizes visibility of the appliance when mounted on a tooth. The ceramic is formed by pressing a powder material, such as high purity aluminum oxide, and sintering to yield a single phase appliance having substantially zero porosity and an average grain size preferably in the range of 10 to 30 microns. The substantially color-free ceramic appliance has desirable strength and other mechanical properties combined with a translucency which permits the natural color of the tooth to diffusely show through in a fashion tending to make the appliance blend with and disappear against the tooth.

43 Claims, 1 Drawing Sheet

U.S. PATENT DOCUMENTS

| | | | |
|---|---|---|---|
| 3,423,833 | 1/1969 | Pearlman | 433/8 |
| 3,464,837 | 9/1969 | McLean et al. | 433/202.1 |
| 3,496,637 | 2/1970 | Etengoff | 433/8 |
| 3,541,688 | 11/1970 | McLean et al. | 427/2 |
| 3,541,688 | 11/1970 | McLean et al. | 433/208 |
| 3,732,087 | 5/1973 | Grossman | 65/33 |
| 3,930,311 | 1/1976 | Andrews | 433/8 |
| 4,097,935 | 7/1978 | Jarcho | 423/633 |
| 4,197,118 | 4/1980 | Wiech, Jr. | 264/63 |
| 4,216,583 | 8/1980 | Reynolds | 433/9 |
| 4,219,617 | 8/1980 | Wallshein | 433/8 |
| 4,281,991 | 8/1981 | Michl et al. | 433/202.1 |
| 4,288,221 | 9/1981 | Engel | 433/202.1 |
| 4,302,532 | 11/1981 | Wallshein | 433/8 |
| 4,310,306 | 1/1982 | Wallshein | 433/9 |
| 4,321,042 | 3/1982 | Scheicher | 433/201.1 |
| 4,322,206 | 3/1982 | Reynolds | 433/9 |
| 4,364,731 | 12/1982 | Norling et al. | 433/218 |
| 4,381,918 | 5/1983 | Ehrnford | 433/202.1 |
| 4,388,069 | 6/1983 | Orlowski | 433/201.1 |
| 4,392,828 | 7/1983 | Ehrnford | 433/201.1 |
| 4,411,625 | 10/1983 | Koblitz et al. | 433/217.1 |
| 4,431,420 | 2/1984 | Adair | 433/202.1 |
| 4,431,421 | 2/1984 | Kawahara et al. | 433/202.1 |
| 4,460,336 | 7/1984 | Smith et al. | 433/9 |
| 4,544,359 | 10/1985 | Waknine | 433/202.1 |
| 4,595,598 | 6/1986 | DeLuca et al. | 427/2 |
| 4,639,218 | 1/1987 | Jones et al. | 433/8 |

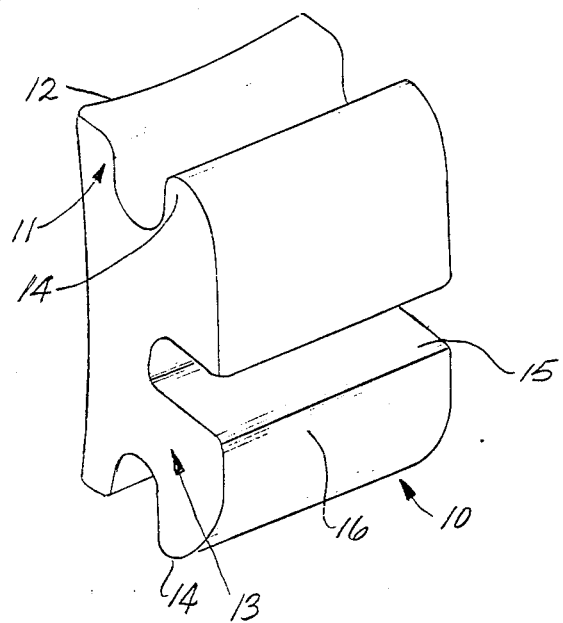

CERAMIC ORTHODONTIC APPLIANCE

Cross-Reference to Related Applications

This is a continuation of application Ser. No. 861,240 filed May 8, 1986 now abandoned.

Background of the Invention

Orthodontic treatment of improperly positioned teeth involves the application of mechanical forces to urge the teeth into correct alignment. The most common form of treatment uses orthodontic brackets which are small slotted bodies configured for direct cemented attachment to the front (labial) or rear (lingual) surfaces of the teeth, or alternatively for attachment to metal bands which are in turn cemented or otherwise secured around the teeth.

A resilient curved arch wire is then seated in the bracket slots, and the arch wire is bent or twisted before installation whereby the restoring force exerted by the seated resilient wire tends to shift the teeth into orthodontically correct alignment. Depending on the shape of the arch wire (both round and rectangular cross sections are in common use) and the orientation of the bracket slot, it is possible to apply forces which will shift, rotate or tip the teeth in any desired direction.

Stainless steel is in many ways an ideal material for orthodontic brackets (and associated tooth bands if banded attachment is used) because this metal is strong, nonabsorbent, weldable, and relatively easy to form and machine. A significant drawback of metal appliances, however, relates to cosmetic appearance when the patient smiles. Adults and older children undergoing orthodontic treatment are often embarrassed by the "metallic smile" appearance of metal bands and brackets, and this problem has led to various improvements in recent years.

One relates to development of adhesives, bracket bases, and techniques for direct cemented attachment of brackets to at least the anterior teeth which are prominently displayed when smiling. Direct cementation eliminates the need for metal toothbands which are a major factor in the metallic-smile problem. Part of this has included development of smaller brackets which are less obtrusive.

Another area of improvement lies in use of lingual brackets which do not show at all from the front. These are not suitable for many situations.

Still another area of improvement involves use of nonmetal materials for the brackets. Plastic orthodontic brackets have come into relatively common use, but plastic is not an ideal material because it lacks the structural strength of metal, and is susceptible to staining and other problems. Some of these problems are solved or alleviated by ceramic materials which have recently been proposed for orthodontic appliances. Both the plastic and ceramic materials present a significantly improved appearance in the mouth, and often the only visible metal component is a thin arch wire which is cosmetically acceptable. It has been proposed to use sapphire or other crystalline material for brackets but transparent ceramics have undesirable prismatic effects and single crystal appliances are subject to cleavage. Other ceramic brackets have been largely opaque so that they either do not match tooth color or require coloring which is uneconomic.

This invention is directed to a ceramic bracket which achieves further cosmetic improvement by having a translucent quality which picks up the color of the underlying tooth to make the bracket blend with the tooth. From the appearance standpoint, the translucent bracket is a significant improvement over both transparent and opaque brackets of nonmetallic construction.

Summary of the Invention

The improvement of this invention relates to orthodontic appliances formed from a polycrystalline ceramic material which is translucent, rather than transparent or opaque. A presently preferred ceramic material is obtained by pressing and sintering ceramic powder which is preferably aluminum oxide. The grain size of the polycrystalline ceramic is in a preferred range of 2 to 50 microns and more specifically 10 to 30 microns. The ceramic body is a nonporous single-phase polycrystalline material with an optical transmittance for visible-light wavelengths in the range of from 20 to 60% and preferably 20 to 40%. The body is of a neutral color which, taken in combination with the important property of translucency, makes the appliance nearly invisible when viewed against the tooth from a relatively short distance. The preferred ceramic material has a modulus of rupture of at least about 40,000 psi to insure adequate strength of the appliance.

Description of the Drawings

FIG. 1 is a pictorial view of an orthodontic bracket made according to the invention.

Description of the Preferred Embodiment

FIG. 1 shows an exemplary orthodontic appliance in the form of an orthodontic bracket 10. The bracket has a base 11 suitable for either direct bonding to a tooth, or attachment to any kind of mounting fixture. A tooth-facing surface 12 of the base 11 is preferably conventionally concavely curved about both a mesiodistal axis and an apical axis to match the natural convexity of the tooth labial surface, but other curvatures can be used to accommodate lingual bracket positioning.

A bracket body 13 extends from the base 11 to define bracket tie wings 14 for ligature anchorage, and a mesiodistally oriented arch-wire slot 15 extending from an outer body surface 16 into the bracket body. The presence or absence of tie wings (of either single- or twin-wing configuration) is not a feature of the invention, and the base and arch-wire slot may be angulated as desired to minimize or eliminate torquing or other bends of the arch wire.

The term "orthodontic appliance" is herein used in a broad sense to include any device intended for mounting on a tooth, and used to transmit to the tooth corrective force from an arch wire, spring, elastic, or other activatable force-applying component. Similarly, the term "arch-wire slot" is used broadly to designate any bracket structure which receives or couples with the force applying component. The term is thus intended to include such equivalent structures as a buccal tube which receives a facebow or similar device.

The orthodontic appliance is translucent since it is a polycrystalline article made of a ceramic material, preferably alpha aluminum oxide. It is important that the ceramic has a high degree of optical transmittance in the visible spectrum, but also that it diffuse the light passing through the appliance. As is well known, human teeth have a broad range of color (quantified, for example, by the commercially available Vita shade system covering the range A1 through D4), and to make the improved orthodontic appliance effectively "disappear" when in place, it should assume the color of the underlying tooth. Thus, the ceramic material should be neutral, and neither add color to the light passing through nor subtract color by appreciable absorption. Aluminum oxide is particularly suitable since its optical transmittance is substantially constant throughout the visible spectrum and it therefore does not change the color of light passing through.

It has been proposed to use transparent sapphire or single crystal aluminum oxide for orthodontic appliances. This material is grown in the form of a single crystal or closely aligned bicrystals having a cross section close to the desired cross section of the appliance. The crystal is grown in rods which are sliced to the size of individual appliances. These can then be cut and shaped to their final form by abrasive grinding. The idea was that the highly transparent appliance would show the tooth color. Such a transparent appliance also has refractive effects and does not fully achieve the desired result. Teeth are neither glossy nor opaque and a transparent appliance may still be quite noticeable.

More significantly, the crystalline material is subject to cleavage under loads that occur in the course of orthodontic treatment. Essentially, point forces of very high magnitude are applied to orthodontic appliances by loading of the associated arch wire and tie wings, and also during chewing. These high point loads can initiate cleavage along crystallographic planes of the sapphire resulting in breakage. A significant shortcoming of crystalline aluminum oxide is a consequence of its manufacturing. Single crystals or large bicrystals or the like may be grown to near net shapes by a modified Czochralski method. However, grinding may be required to form the base, the arch wire groove or other surfaces. The grinding introduces surface imperfections which can have a devastating effect on strength. Cracks initiating at such imperfections propagate through the crystal resulting in breakage at abnormally low stresses, well below the stresses one would expect.

Further, growth of crystalline sapphire and subsequent machining operations to complete the orthodontic appliances are costly operations with little prospect of manufacturing economies. Growing crystalline sapphire is quite slow, and meeting the quantities required for commercial embodiments may not be feasible.

It is desirable that the appliance be translucent rather than transparent. Light passes through a transparent ceramic in a straight line. Thus, when a crystalline sapphire is placed on a printed page, the text can be read through the crystal. In a translucent material, a large proportion of light passes through the crystal but not in a straight path. Optical irregularities in the bulk material cause the light passing therethrough to be refracted, reflected, and otherwise scattered so that it is diffuse. One could not read this printed page through a completely translucent material.

Translucence is a relative property of a material. This can be visualized by considering water to which milk is added. When a few drops of milk are added to the water, it becomes cloudy or milky. The formerly completely transparent water is now somewhat translucent in that a portion of the light transmitted through the solution is diffused by scattering from the milk particles. As more milk is added, more of the light is diffused until it becomes impossible to read through the solution. Further, the solution takes on the color of the milk as more light entering the front of the solution is backscattered by the milk particles and less is reflected from whatever surface is behind the solution. When the solution is slightly cloudy an overwhelming proportion of the light emitted from the face of the solution is reflected from the surfaces behind the solution and a minor proportion is backscattered by particles of milk within the solution.

It is significant that the translucence be a bulk property of the material rather than a surface effect. Some light diffusion can be obtained by roughening a surface as, for example, with frosted glass. This is not completely satisfactory in an orthodontic appliance, however, since the surface is continually wet, and the principal change in the index of refraction occurs at the air-liquid interface which is nearly smooth. Further, it is undesirable to have roughened surfaces on orthodontic appliances because of the adhesion of substances in the mouth. As pointed out above, rough surfaces may also have imperfections which serve as a source for initiation of cracks. Since ceramics do not have the ductility of metals, roughness can significantly degrade strength.

To minimize the contrast between the appliance and the tooth, it should have the same color as the tooth. Color is perceived due to light reflected from a surface. One could form a spectrum of appliances to match the range of natural tooth colors, but the cost and inconvenience would be undesirable. It is better to see the tooth color itself, as seen through a translucent appliance.

In order for the orthodontic appliance to assume the color of the underlying tooth, it is important that sufficient light seen from the front surface of the appliance attached to the tooth be light that has been transmitted from the tooth surface, that the tooth color is not overwhelmed by light backscattered from optical irregularities within the appliance. In other words, a substantial amount of the incident light should pass through the appliance, albeit diffused, to the base for reflection off of the tooth surface, and then be retransmitted through the appliance to be emitted from the front surface. Since the appliance is translucent rather than transparent, a portion of the light is backscattered by the internal optical irregularities in the appliance. The backscattering is preferably minimized since the backscattered light tends to be white and will almost invariably be different from the tooth color. Further, by using a translucent ceramic appliance, all of the optical properties of the tooth are mimicked. Teeth are not opaque and considerable attention has been devoted to achieving limited translucence in materials used for prostheses to mimic the replaced or repaired tooth. Such concern is alleviated by a translucent appliance since light transmitted through the tooth as well as that light reflected from the front, is, in turn, emitted unchanged from the translucent appliance.

The amount of visible light transmitted through the polycrystalline ceramic used to make the appliance is in the range of from 20% to 60%, and the light backscattered from internal optical irregularities within the appliance is in the range of from 40% to 80%. Preferably the transmitted light is in the range of from 20% to 40% and the backscattered light is in the range of from 60% to 80%. This translucence is measured by in-line transmission of light through a specimen 0.5 mm thick, the light being in the wavelength range of from 0.4 to 0.8 microns. This translucence assures that the light seen from the front surface includes sufficient light that has been reflected from the tooth surface to take on the color of the underlying tooth.

The translucence measurement is made by illuminating a sample 0.5 mm. thick with a collimated beam and measuring the proportion of light emitted at the opposite surface of the sample in the direction of the collimated beam. Since the light is scattered by the optical irregularities within the sample, a small proportion may be transmitted in the direction of the incident beam and a large proportion scattered in other directions. This is to be distinguished from a transmittance measurement where much of light is absorbed by the medium through which it passes. The scattering is desirable in the orthodontic appliance since it conveys the color of the underlying tooth and diffuses it without prismatic effects. Aluminum oxide has little absorption and the limited absorption is uniform throughout the visible spectrum so that no color change is introduced.

In a preferred embodiment, translucence is obtained in an orthodontic appliance by forming it from a polycrystalline ceramic that is inherently transparent. By polycrystalline is meant that the appliance is made of a ceramic having a multiplicity of randomly oriented crystals self-bonded together. That is, the adjacent crystals are separated by a grain boundary of the same material as the crystals, rather than being cemented together by a different material. The pressed and sintered product is chemically homogeneous. The polycrystalline ceramic has a single phase and substantially zero porosity to maintain a high degree of optical transmittance. It is preferably made of high purity ceramic such as 99.95% alpha aluminum oxide.

The appliance may have a small amount of residual porosity. It appears that the polycrystalline aluminum oxide has a density of at least 99.5% of the theoretical density of single crystal alpha aluminum oxide. It is not known if this difference is residual porosity or a consequence of decreased density of the arrays of disorder along the multiplicity of grain boundaries in the fine grained polycrystalline material.

The average grain size of the polycrystalline material is larger than the wavelength of visible radiation so that it retains a high degree of transmittance without interference effects. The grain size is small enough that crystallographic cleavage will not propagate through the thinner sections of a representative orthodontic appliance. Preferably the grain size is no more than 10% of the thickness of the thinnest section of the appliance, and most particularly less than 6% of the thinnest section. The thinnest section that bears any substantial load might, for example, be a gingival tie wing. This thickness is many times the average grain size. Thus, any line through the appliance would encounter a plurality of crystals or grains.

A preferred orthodontic appliance is made by pressing and sintering aluminum oxide. The parts are fabricated by pressing powder to a desired shape and sintering the pressed compact at temperatures close enough to the melting point of the aluminum oxide that the ceramic coausces and densifies. In one such manufacturing technique, high purity aluminum oxide powder is placed in the die cavity of a high-pressure hydraulic press. Submicron size particles are used. This provides an active sintering process and allows one to achieve substantially theoretrical density in the sintered compact.

The die has a cavity with a cross section corresponding to the desired cross section of the appliance being formed. The arch wire groove in the appliance may be completely or partially formed in this operation, or may be ground later. A punch having the cross section of the die cavity is pressed into the powder in the cavity at 10,000 to 20,000 psi to tightly pack it. In a preferred embodiment, a lateral slide is also employed for forming the curved base of the appliance. Such punches, dies, and slides are conventionally used for pressing a broad variety of metals or ceramics to desired shapes. Preferably, multiple die cavities are used in commercial operations for high productivity. Alternatively, such powder may be placed in a latex mold and isostatically pressed at 20,000 to 45,000 psi to form a green compact. In still another technique the green compact is made by "injection molding" the powder by conventional means at about 15,000 psi.

After pressing the powder, the green compact, which is rather fragile, is ejected from the die or mold. To give the compact some green strength, a small amount of a temporary organic binder such as a paraffin wax or polyethylene glycol may be included by coating particles with the binder. From 1.1% to 13% by weight of binder may be applied by milling the organic binder with the ceramic, either dry or in a solvent such as hexane in the case of a wax, or water or alcohol in the case of polyethylene glycol. Such wax vaporizes in subsequent operations and, if desired, a conventional vacuum dewaxing step can be included. Binder can be removed by heating to temperatures of 400 to 600° C. in vacuum or up to atmospheric pressure.

The compact is sintered at temperatures from 1750° C. to 2050° C. for 30 to 60 minutes in a hydrogen atmosphere. At such sintering temperatures, aluminum oxide so that the original particles of aluminum oxide powder coalesce together and form a dense polycrystalline article having an average grain size in the range of from about two to fifty microns. The time and temperature should be controlled so that the average grain size in the completed orthodontic appliance is in this range for high optical transmittance and strength. If the average grain size is less than about two microns, optical effects due to adjacent grain boundaries may interfere with good light transmission through the appliance. If the average grain size is larger than about fifty microns, strength may be reduced due to the greater distances through which cracks may propagate before encountering a grain boundary. Preferably the average grain size of the polycrystalline ceramic is in the range of from ten to thirty microns for optimum transmission of light and strength with reasonable processing conditions and times.

If desired, the appliance can be "HIPed" (hot isostatic pressed) to increase its density. Hot isostatic pressing (HIPing) is a relatively recent advance in high density pressing of metals and ceramics. In such a press, isostatic pressure is applied while the part being HIPed is heated to the sintering temperature. The combination of high temperature and high pressure compacts the part to have substantially zero porosity.

In the case of alpha aluminum oxide, orthodontic appliances are HIPed at a pressure in the order of 15,000 psi, and heated to a temperature of about 1750 to 2050° C. for a period of up to an hour. The sintering temperature is a little below the melting point of alpha aluminum oxide.

The sintered polycrystalline aluminum oxide orthodontic appliance is translucent. The in-line optical transmittance through the polycrystalline alumina is in the range of from 20 to 60% and preferably 20 to 40%. Light passing through the appliance is, however, diffused by the translucent polycrystalline aluminum oxide. It appears that the optical transmittance in an in-line transmittance test through 0.5 mm thickness of polycrystalline aluminum oxide having a density of about 99.5% of theoretical density, an average grain size of about 20 microns and a surface roughness of about 5 microinches RMS is about 53%.

The reason light passing through the polycrystalline aluminum oxide is diffused is not completely known. Since the material is polycrystalline, adjacent crystals have different, largely random crystallographic orientations. This results in variations in index of refraction along any straight-line path through the appliance. Small refractive effects may occur at grain boundaries, resulting in a multiplicity of internal scattering locations. The grain boundaries are sites of crystallographic imperfections and these arrays of imperfections may also have different indexes of refraction which deflect light in a multiplicity of directions. Further, even though the ceramic after sintering has substantially zero porosity, traces of residual porosity may remain in grain boundaries or other locations in the finished product. Such traces of porosity would have a pronounced effect on light transmission, with resultant scattering and diffusion of light passing through the polycrystalline material. It is probable that a combination of these effects is involved in producing the desired degree of translucence in a pressed and sintered aluminum oxide orthodontic appliance.

It is significant that the appliance has a high degree of optical transmittance, which is believed due to the self bonding of high purity aluminum oxide in the polycrystalline material. It has been proposed in the past to form ceramic orthodontic appliances by pressing and cementing aluminum oxide powder. In that technique, aluminum oxide powder is commingled with other ceramic materials having a lower melting point than the aluminum oxide. The mixed powders are pressed in a hydraulic press and the resultant green compacts are sintered at about the melting temperature of the other ceramic phase. The resultant liquid bonds the aluminum oxide particles together, forming a relatively dense and strong ceramic. This liquid phase bonding is often referred to in the jargon as "sintering" whereas it is more properly referred to as "cementing", since the individual aluminum oxide particles are cemented together by a second ceramic phase. The aluminum oxide may not recrystallize in this process.

As a result of such processing, an orthodontic appliance is milk white. It may not be opaque since the inherent transparency of components used in the manufacture will commonly let some light be transmitted through such an appliance. Liquid phase cementing may occur in porcelains, for example, and they have a slight degree of translucence. The degree of optical transmittance is, however, quite low and most of the light seen is reflected or backscattered from the surface in view. This results in a milky white appearance where the ceramic has its own "color" albeit white. Such color cannot, of course, match the range of colors in human teeth. Colorants have been added to dental prostheses to match adjacent teeth. The cost of having an inventory of orthodontic appliances to match the color range in teeth is prohibitive.

In addition to the translucency achieved by the optical irregularities mentioned above, other ways of diffusing light or inducing translucency in a transparent polycrystalline ceramic material may be employed. As mentioned above, translucency may occur due to random changes in crystallographic orientation of the small grains in the polycrystalline material. It may be due to arrays of imperfections and grain boundaries or the like. Diffusion may occur due to traces of porosity remaining in the ceramic. If desired, translucency may be induced by doping the ceramic with tiny amounts of other substances that serve as scattering sites; many impurities tend to diminish transparency of crystalline ceramics. Imperfections may be produced by radiation or ion bombardment. The degree of translucency is more significant than the technique for achieving translucency.

Although aluminum oxide is a preferred material for construction of a translucent orthodontic appliance, other materials may be employed. Aluminum oxide is desirable since it is strong, hard, transparent, has neutral color, is inexpensive and readily available. If desired, up to about one percent magnesium oxide may be added to the aluminum oxide for aiding in sintering and enhancing strength of the aluminum oxide. Translucent orthodontic appliances may also be fabricated of polycrystalline magnesium-aluminum spinel ($MgAl_2O_4$), zirconium oxide, yttrium aluminum garnet, zirconium silicate, or other strong transparent crystalline materials.

The preferred material for the polycrystalline ceramic orthodontic appliance is high purity alpha aluminum oxide. A purity of 99.95% aluminum oxide is desirable for maximum strength and complete freedom from chromatic effects. Commencing with such pure material increases the tolerance for contamination which may occur in manufacturing operations, although reasonable measures should be taken to avoid introduction of impurities.

A significant reason for using ceramic for forming an orthodontic appliance is the mechanical properties of many ceramic materials. This can be distinguished from the relatively low order properties available in organic materials such as plastics which may also be translucent. It is preferred that the ceramic material have a modulus of rupture of at least 40,000 psi and preferably at least 60,000 psi. A modulus of elasticity of at least $20 \times 10^6$ psi and a hardness of at least 7 on the Mohs scale are also preferred. Modulus of rupture is probably the more significant mechanical property in the brittle ceramic materials used for fabrication of translucent polycrystalline ceramic orthodontic appliances.

A ceramic orthodontic appliance is secured to a tooth with an adhesive substance. Good bonding of the adhesive to the base of the appliance is important so that it can withstand high occlusal forces and the stress of orthodontic correction. Controlled roughness of the base of the appliance may therefore be desirable to enhance bonding strength of the adhesive to the appliance.

As mentioned above, a polycrystalline ceramic orthodontic appliance may be made by compressing powder in a die. A cross slide is used in the die to form the curved base of the appliance. It is preferred to form the face of the slide with controlled roughness to produce a desired roughness on the base of the appliance. In particular, it is desirable to form tiny pyramidal projections on the face of the slide for forming pyramidal pits in the appliance base. Such pyramidal protrusions may be ground on the face of the slide or formed by electrical discharge machining. Roughness of the base may also be provided in parts made by isostatic pressing or injection molding by control of the mold surface.

Other surfaces of the orthodontic appliance should be smooth. Smoothness is promoted by employing polished dies and punches in the pressing operation. The surfaces may be smoothed by grinding, ultrasonic or abrasive polishing after sintering. Conventional flux polishing may also be used. In one such technique the appliance is immersed for up to thirty minutes in molten flux: at a temperature in the range of 850 to 900° C. An exemplary flux has about 51% by weight $LiBO_2$, 13% $Li_2B_4O_7$, 20% LiF, and 16% $Al_2O_3$. Residual flux can be removed with aqueous HF. A surface having a roughness of up to three to five microinches RMS is preferred.

The pressing and sintering technique for forming a polycrystalline ceramic article from ceramic powder can result in an orthodontic appliance with rather precise dimensions. Precision is enhanced by careful control of the pressing operation for forming green compacts and the mix of particle sizes in the ceramic powder. The sintering operation inherently causes shrinkage from the green compact to the finished article. The proportion of shrinkage can be known from carefully controlled particle size, mold geometry and pressure in green compact pressing. Care in these conventional techniques can produce finished orthodontic appliances well within acceptable tolerance limits. The most critical tolerance on the orthodontic appliance is the archwire groove. If desired the groove may be ground into the appliance after pressing and sintering. Such grinding can be expedited by pressing in an undersized groove that is enlarged to the final desired configuration by grinding.

Polycrystalline aluminum oxide of high density and suitable translucency and strength for making orthodontic appliances in practice of this invention may be made by a variety of vendors including Ceradyne, Inc., Santa Ana, California; Coors Porcelain, Golden, Colorado; and the Lucalox division of General Electric Company, San Francisco, California.

An alternative manufacturing technique may be used in the initial forming of the green compact of aluminum oxide powder. Powder mixed with a small amount of temporary binder can be extruded in a bar with a cross section close to the desired cross section. This bar can then be sliced to form individual appliances, either before or after sintering. Parts of the appliance, such as the base, may be machined on such an extruded appliance, either before or after sintering.

What is claimed is:

1. A translucent polycrystalline ceramic orthodontic appliance having an in-line transmittance of visible light through 0.5 millimeter thickness in the range of from 20 to 60 percent.

2. An orthodontic appliance as recited in claim 1 wherein the ceramic has neutral color.

3. An orthodontic appliance as recited in claim 1 wherein the ceramic has a modulus of rupture of at least 40,000 psi.

4. An orthodontic appliance as recited in claim 1 wherein the translucence is produced by random variations in crystal orientation within the appliance.

5. An orthodontic appliance as recited in claim 1 wherein the ceramic has a single phase and substantially zero porosity.

6. An orthodontic appliance as recited in claim 1 wherein the ceramic consists essentially of aluminum oxide.

7. An orthodontic appliance as recited in claim 6 wherein the ceramic is at least 99.95% aluminum oxide.

8. An orthodontic appliance as recited in claim 1 wherein the transmittance is in the range of from twenty to forty percent.

9. An orthodontic appliance as recited in claim 1 wherein the ceramic has an average grain size in the range of from ten to fifty microns.

10. An orthodontic appliance as recited in claim 9 wherein the average grain size is in the range of from 10 to 30 microns.

11. A translucent orthodontic appliance as recited in claim 1 single phase polycrystalline ceramic having an average grain size larger than the wavelength of visible light and no more than ten percent of the thickness of the thinnest section of the appliance.

12. An orthodontic appliance as recited in claim 11 wherein the ceramic consists essentially of 99.95% aluminum oxide.

13. An orthodontic appliance as recited in claim 11 wherein the ceramic has substantially 100% of theoretical density and has substantially zero porosity.

14. An orthodontic appliance as recited in claim 11 the ceramic has a modulus of rupture of at least 40,000 psi.

15. An orthodontic appliance as recited in claim 11 wherein the ceramic is selected from the group consisting of aluminum oxide, $MgAl_2O_4$, zirconium oxide, zirconium silicate, and yttrium aluminum garnet.

16. A translucent orthodontic appliance formed of polycrystalline ceramic having an average grain size in the range of from two to fifty microns and wherein the in-line transmittance of visible light through the appliance is in the range of from 20% to 60% per 0.5 millimeter thickness.

17. An orthodontic appliance as recited in claim 16 wherein the average grain size is in the range of from ten to thirty microns.

18. An orthodontic appliance as recited in claim 16 wherein the transmittance is in the range of from 20% to 40% per 0.5 millimeter thickness.

19. A translucent orthodontic appliance consisting essentially of self-bonded transparent aluminum oxide crystals having a sufficiently small average grain size to diffuse light passing through the appliance and wherein visible light emitted from the front surface of the appliance comprises light backscattered from within the appliance and light transmitted through the appliance from the appliance base, the in-line transmittance through the appliance being in the range of from twenty to sixty percent per 0.5 millimeter thickness.

20. An orthodontic appliance as recited in claim 19 wherein the average grain size is in the range of from 10 to 30 microns.

21. An orthodontic appliance as recited in claim 19 wherein at least the front surface of the orthodontic appliance has a surface finish no rougher than about five microinches RMS.

22. A translucent orthodontic appliance formed of polycrystalline ceramic that is transparent, but having sufficient optical irregularities on any straight path through the appliance to diffuse light passing through the appliance wherein visible light emitted from the front surface of the appliance comprises light backscattered from within the appliance and light transmitted through the appliance from the appliance base, the in-line transmittance through the appliance being in the range of from 20% to 60% per 0.5 millimeter thickness.

23. An orthodontic appliance as recited in claim 22 wherein the optical irregularities are produced by random variations in crystal orientation within the appliance.

24. An orthodontic appliance as recited in claim 22 wherein the optical irregularities are produced by traces of residual porosity in the appliance.

25. An orthodontic appliance as recited in claim 22 wherein the optical irregularities are produced by grain boundaries in the appliance.

26. An orthodontic appliance as recited in claim 22 wherein the optical irregularities are produced by arrays of crystallographic imperfections in the appliance.

27. An orthodontic appliance as recited in claim 22 wherein the optical irregularities are produced by doping the ceramic crystals with foreign atoms.

28. An orthodontic appliance as recited in claim 22 wherein the optical irregularities comprise random variations of index of refraction.

29. An orthodontic appliance as recited in claim 22 wherein the ceramic consists essentially of aluminum oxide.

30. A translucent orthodontic appliance formed of a polycrystalline ceramic wherein a portion of visible light emitted from the front surface of the appliance is light transmitted from the appliance base and a portion of the light is internally backscattered from internal optical irregularities within the appliance, the quantity of internal optical irregularities within the appliance being sufficient that no substantial portion of the light from the base of the appliance reaches the front surface in a straight line path therebetween, wherein the appliance has an in-line transmittance of visible light in the range of from twenty to sixty percent per 0.5 millimeter thickness.

31. An orthodontic appliance as recited in claim 30 wherein the ceramic consists essentially of aluminum oxide.

32. A translucent orthodontic appliance as recited in claim 30 wherein the ceramic comprises aluminum oxide and has substantially 100% of theoretrical density 33. An orthodontic appliance as recited in claim 32 wherein the aluminum oxide has an average grain size in the range of from ten to fifty microns.

34. An orthodontic appliance as recited in claim 46 wherein the average grain size is in the range of from ten to thirty microns.

35. A translucent orthodontic appliance for coupling to a tooth surface, formed of a single phase, self-bonded, polycrystalline ceramic having substantially randomly oriented crystals with an average grain size larger than the wavelength of visible light and no more then ten percent of the thickness of the thinnest section of the appliance, said crystals scattering visible light passing through said appliance while having an in-line transmittance of visible light of at least 20% through 0.5 millimeter thickness of ceramic for minimizing backscattering of said visible light, whereby said visible light passing through said appliance is reflected from said tooth surface and retransmitted back through said appliance for emission therefrom, wherein said appliance substantially assumes a color corresponding to said tooth surface.

36. An orthodontic appliance as recited in claim 35 wherein the ceramic consists essentially of aluminum oxide which is at least 99.95% pure.

37. An orthodontic appliance as recited in claim 35 wherein the ceramic has substantially 100% of theoretrical density and has substantially zero porosity.

38. An orthodontic appliance as recited in claim 35 wherein the ceramic has a modulus of rupture of at least 40,000 psi.

39. An orthodontic appliance as recited in claim 35 wherein the ceramic is selected from the group consisting of aluminum oxide, $MgAl_2O_4$, zirconium oxide, zirconium silicate, and yttrium aluminum garnet.

40. A translucent polycrystalline ceramic orthodontic bracket formed from self-bonded alpha aluminum oxide for coupling to a tooth surface, having translucence defined by an in-line transmittance of visible light of at least 20% through 0.5 millimeter thickness of ceramic, whereby said transmittance is sufficient to (1) scatter light passing therethrough, (2) minimize backscattering of light toward a front surface of the bracket, and (3) retransmit said light reflected from said tooth surface for emission from said bracket, said bracket thereby substantially assuming a color corresponding to said tooth surface.

41. An orthodontic appliance as recited in claim 40 wherein the ceramic has a single phase and substantially zero porosity.

42. A translucent ceramic orthodontic bracket for coupling to a tooth, formed from a self-bonded polycrystalline structure having sufficient strength for withstanding loads applied during orthodontic correction, and sufficient translucency defined by an in-line transmittance of visible light, wherein visible light emitted from the front surface of the bracket comprises a first portion backscattered from within the bracket, and a second portion reflected from a portion of said tooth underlying said bracket and retransmitted back through said bracket, said in-line transmittance of visible light being of at least 20% through 0.5 millimeter thickness of ceramic and being sufficient to (1) scatter light passing therethrough, and (2) substantially minimize said backscattered visible light, whereby said bracket substantially assumes a color corresponding to said tooth.

43. A method of providing a true color visual effect of a tooth having an orthodontic ceramic bracket mounted thereon, comprising the steps of:
    passing light through said bracket to the surface of said tooth, said light passing through said ceramic bracket being scattered, said ceramic bracket having a predetermined translucency defined by an in-line transmittance of visible light of at least 20% through 0.5 millimeter of ceramic;
    reflecting said scattered light from said tooth; and,
    passing said reflected and scattered light through said bracket to attain the visual effect of the true color of said tooth.

* * * * *

UNITED STATES PATENT AND TRADEMARK OFFICE
CERTIFICATE OF CORRECTION

PATENT NO.   :   4,954,080

DATED        :   September 4, 1990

INVENTOR(S)  :   John S. Kelly, Henrick K. Gille and John A. Negrych

It is certified that error appears in the above-identified patent and that said Letters Patent is hereby corrected as shown below:

Title page, item [75], add John A. Negrych of Westminster, California as an inventor Col. 6, Line 33, after the word oxide, add -- sinters --

Col. 10, Line 16, after the numeral 1, add -- formed of a --

Col. 10, Line 26, after the numeral 11, add -- wherein --

Signed and Sealed this

Nineteenth Day of May, 1992

Attest:

DOUGLAS B. COMER

*Attesting Officer*      *Acting Commissioner of Patents and Trademarks*